United States Patent [19]

Schreiber

[11] 4,322,537
[45] Mar. 30, 1982

[54] TERTIARY AMINE OXIDATION AND PRODUCTS THEREOF

[75] Inventor: Stuart L. Schreiber, Somerville, Mass.

[73] Assignee: President and Fellows of Harvard College, Cambridge, Mass.

[21] Appl. No.: 155,059

[22] Filed: Jun. 2, 1980

[51] Int. Cl.³ .................... C07D 213/54; C07C 97/03
[52] U.S. Cl. ................................. 546/315; 564/468; 564/509
[58] Field of Search ..................... 564/468; 546/315

[56] References Cited
PUBLICATIONS

Leonard et al. (1957), *J. Am. Chem. Soc.*, 79, 5279.
Damico et al. (1966), *J. Org. Chem.*, 31, 1607.
Jones et al. (1925), *J. Am. Chem. Soc.*, 46, 1343.
Meerwein et al. (1960), *Justus Liebigs Ann. Chem.*, 635, 1.
Volz et al. (1971), *Justus Liebigs Ann. Chem.*, 752, 86.
Horner et al. (1957), *Justus Liebigs Ann. Chem.*, 597, 20.

*Primary Examiner*—Alan L. Rotman

[57] ABSTRACT

Tertiary amines in which at least one group bonded directly to the nitrogen atom is alkyl of 2 to 20 carbon atoms or in which two or more groups bonded directly to the nitrogen atom together are alkylene of 4 to 7 carbon atoms, are oxidized by trihaloacetyl anhydride or trihaloacetyl halide to mono- and di-trihaloacetylated alpha, beta-enamines.

10 Claims, No Drawings

TERTIARY AMINE OXIDATION AND PRODUCTS THEREOF

The invention described herein was made in part in the course of work under a grant from the National Institute of Health and from the National Science Foundation.

This invention relates to the oxidation of certain tertiary amines, and pertains more specifically to the oxidation of tertiary amines in which at least one group bonded directly to the nitrogen atom is alkyl of 2 to 20 carbon atoms, straight or branched chain, or in which two or more groups together are alkylene of 4 to 7 carbon atoms, by reaction with trihaloacetic anhydride or trihaloacetyl halide to form an acylated alpha, beta-enamine.

Although tertiary amines and acid anhydrides have long been employed in a variety of synthetic transformations, no redox reactions between them have been reported.

It has now been found that tertiary amines in which at least one group bonded directly to the nitrogen atom is alkyl of 2 to 20 carbon atoms or in which two groups bonded directly to the nitrogen atom together are alkylene of 4 to 7 carbon atoms enter into a redox reaction with trihaloacetic anhydride or trihaloacetyl halide to form an acylated enamine in which the unsaturation is in a position alpha, beta to the nitrogen atom and which is either mono- or di-trihaloacetylated, depending upon the particular amine employed and the conditions under which the reaction is carried out. The acylated enamine can enter into a variety of reactions; it can be hydrolyzed, for example, to form the corresponding secondary amine. The oxidation reaction of the present invention thus provides, in combination with a subsequent hydrolysis reaction, a convenient procedure for converting certain tertiary amines into secondary amines. More particularly, in the case of the preferred class of tertiary alkyl amines in which each alkyl group has from 2 to 20 carbon atoms, the acylated enamine is trihaloacetylated dialkyl alkenamine.

The reaction can be represented by the following general reaction scheme:

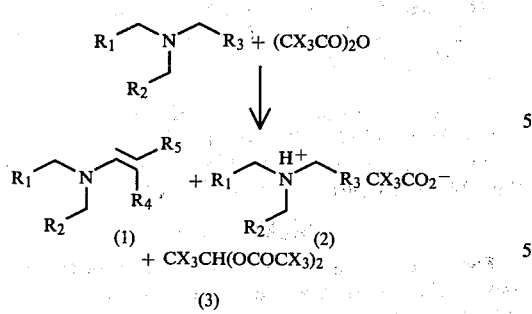

in which $R_1$ and $R_2$ is each hydrogen or an alkyl or aralkyl group of 1 to 19 carbon atoms, and $R_3$ is an alkyl group having 1 to 19 carbon atoms, or in which any two or more of $R_1$, $R_2$ and $R_3$ are joined to form alkylene of 4 to 7 carbon atoms, the remaining R being hydrogen or alkyl or aralkyl having 1 to 19 carbon atoms, X is halogen such as bromine, chlorine or fluorine, preferably fluorine, $R_4$ is hydrogen, alkyl having 1 to 18 carbon atoms, or $CX_3CO-$, and $R_5$ is $CX_3CO-$. An important subclass of amines to which the present invention can be applied is the one in which each of $R_1$, $R_2$ and $R_3$ is alkyl of 1 to 19 carbon atoms. The relative amounts of the acylated enamine (1), amine salt (2), and acetal (3) products depends upon the relative proportions of the starting materials as well as the conditions under which the reaction is carried out. The reaction proceeds in analogous fashion when trihaloacetyl halide, such as trihaloacetyl chloride, is substituted in equivalent amounts for the anhydride; the corresponding halogen acid may be produced as a by-product, or halogen may replace one of the haloacetoxy groups in the acetal by-product (3). The desired product in each case is a trihaloacetylated alpha, beta-enamine, and the trihaloacetyl group in each case is in the beta position adjacent the double bond. The alkyl groups may contain a variety of substituent groups, as in the case of aralkyl groups or substituted aralkyl groups, provided the substituent groups are unreactive with the anhydride or acyl halide.

The temperature at which the reaction is carried out is not critical. Ordinary room temperature can be used, or temperatures as low as 0° C. or even lower, or higher temperatures up to 100° C. or the reflux temperature of the solvent employed as a reaction medium. Generally, temperatures from 0° to 25° C. are preferred.

The reaction can be carried out in any convenient liquid solvent which is inert to the reagents, such as methylene chloride, ethylene chloride, chloroform, ethyl chloride, ethyl ether, tetrahydrofuran, dioxane or the like.

The relative proportions of amine and anhydride employed may vary considerably. When equimolar proportions are used or when an excess of anhydride is employed, the diacylated enamine product (1) is usually obtained along with the amine salt product (2). When a molar excess of amine is used, a mixture of di- and mono-acylated enamine product (1) is usually obtained, the diacylated product predominating. When the $R_1$, $R_2$ and $R_3$ groups each contain three or more carbon atoms, there is obtained only a monoacylated alpha, beta-enamine. Among the amines which can be employed in the process of the present invention are ethyldimethyl amine, triethylamine, diisopropylethyl amine, triisopropyl amine, tri-n-butyl amine, trilauryl amine, stearyldimethyl amine, N-methyl pyrrolidine, N-methyl piperidine, hexamethylene imine, and amines of the formulas:

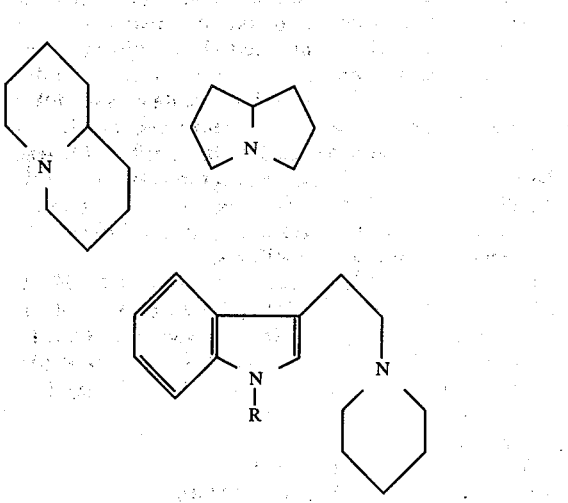

R = 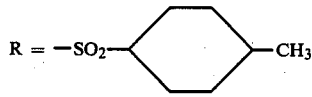

By employing additional base (other than amines), preferably an inorganic base, in the reaction, the amine can be liberated from the amine salt product (2) and recycled in the reaction, leading to higher yields of the acylated enamine product (1) based on the amount of amine starting material. When sufficient additional base is present, conversion of the amine to the desired acylated enamine product (1) can be essentially quantitative. Among suitable bases for this purpose are sodium hydride, potassium hydride or other alkali metal hydrides, sodium hydride being preferred. The exact amount of additional base needed for quantitative conversion of the amine to product (1) depends upon the amount of amine salt formed under the conditions chosen, an amount of base in excess of that equivalent to the amine salt being required. Lesser amounts of additional base lead to recycling of only a portion of the amine salt product.

The following specific examples are intended to illustrate more fully the nature of the invention and not to act as a limitation upon its scope.

EXAMPLE 1

4 Et$_3$N + 4 (CF$_3$CO)$_2$O ⟶

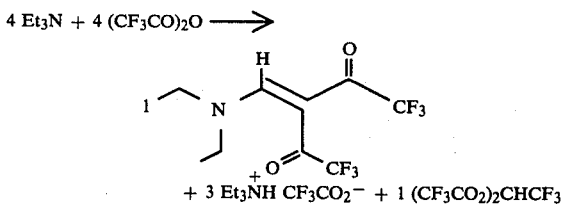

+ 3 Et$_3$NH CF$_3$CO$_2^-$ + 1 (CF$_3$CO$_2$)$_2$CHCF$_3$

A dry 10 ml round bottom flask fitted with a septum and containing an argon atmosphere was charged with 5 ml methylene chloride (distilled from C$_a$H$_2$), 0.70 ml triethyl amine (5 m mole) and cooled to 0° C. with an ice bath. There was added dropwise via syringe 0.71 ml of trifluoroacetic anhydride (5 m mole) with stirring. Stirring was continued for 10 minutes, then the solution was allowed to warm to room temperature and quenched with 1 N hydrochloric acid. The methylene chloride layer was collected and the acid layer was extracted twice with 5 ml methylene chloride. The combined extracts were washed with sodium bicarbonate solution, dried with sodium sulfate and rotoevaporated to give 0.38 g. of a yellow oil, which was pure (1) by TLC and NMR. Further purification was effected by SiO$_2$ column chromatography or by Kugelrohr distillation. (90° C. at 0.2 mm). By distillation an analytically pure sample was obtained. Analytical data for the pure sample was as follows:

$^1$H NMR: (δ, CDCl$_3$, Me$_4$Si standard): 7.63 (1H, s), 3.60 (2H, q, J=7 Hz), 3.25 (2H, q, J=7 Hz), 1.40 (3H, t, J=7 Hz), 1.15 (3H, t, J=7 Hz); $^{13}$[NMR: (δ, CDCl$_3$, Me$_4$Si standard): 180.4 (q, J$_{c-f}$=35.3 Hz), 156.9 (d), 116.8 (q, J$_{c-f}$=290.8 Hz), 101.4 (s), 55.1 (t), 47.0 (t), 14.7 (q), 10.8 (q).

IR: 1690, 1645, 1595 cm$^{-1}$
UV: λ$_{max}$=284 nm, ε$_{max}$=23,000
MS: m/e (rel %): 291 (56), 222 (100)

Analysis: Calculated for C$_{10}$F$_6$H$_{11}$NO$_2$: C: 41.25, H: 3.81, N: 4.81; Found: C: 40.94, H: 3.91, N: 4.72.

EXAMPLE 2

The same procedure was followed as in Example 1 except that there was used as the amine 0.30 ml diisopropylethyl amine (1.72 m moles) and there was used 0.32 ml of trifluoroacetic anhydride (1.3 eq.). There was obtained 130.2 mg of the desired product:

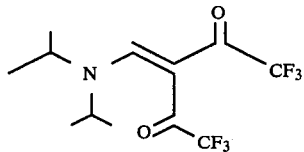

Analytical data for the product was as follows:
$^1$H NMR: (δ, CDCl$_3$, Me$_4$Si standard): 7.72 (1H, s), 3.80 (1H, septet, J=7 Hz), 3.75 (1H, septet, J=7 Hz), 1.40 (6H, d, J=7 Hz), 1.35 (6H, d, J=7 Hz)
IR: 1700, 1625, 1595 cm$^{-1}$
UV: λ$_{max}$=287 nm, ε$_{max}$=19,200
MS: m/e (rel %): 319 (50), 250 (100)
Analysis: Calculated for C$_{12}$H$_{15}$F$_6$NO$_2$: C: 45.15, H: 4.74, F: 35.71, N: 4.39. Found: C: 45.39, H: 4.85, F: 35.53, N: 4.27.

EXAMPLE 3

The same procedure was followed as in Example 1 except that there was used as the amine 0.3 ml N-methyl piperidine (2.47 m moles), there was used 0.45 ml of trifluoroacetic anhydride (1.3 eq.), and the reaction mixture was stirred for 24 additional hours at room temperature before quenching. The desired product was obtained in good yield:

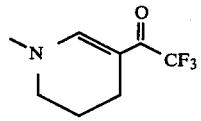

Analytical data for the product was as follows:
$^1$H NMR: (δ, CDCl$_3$, Me$_4$Si standard): 7.49 (1H, s), 3.21 (2H, t, J=7 Hz), 3.11 (3H, s), 2.34 (2H, t, J=7 Hz), 1.85 (2H, quintet, J=7 Hz)
IR: 1590 cm$^{-1}$
UV: λ$_{max}$=304 nm, ε$_{max}$=27,623
MS: m/e (rel %): 193 (60), 124 (100)
Analysis: Calculated for C$_8$H$_{10}$F$_3$NO: C: 49.74 H: 5.22 N: 7.25. Found: C: 49.65 H: 5.26 N: 7.17.

EXAMPLE 4

The same procedure was followed as in Example 1 except that there was substituted for trifluoroacetic anhydride the equivalent amount of trifluoroacetyl chloride. The same product (1) was obtained in good yield.

EXAMPLE 5

The same procedure was followed as in Example 1 except that 10 ml of methylene chloride was used instead of 5, the amount of trifluoroacetic anhydride was 4.0 ml, and there was added 2.0 g sodium hydride (oil free). The reaction mixture was stirred for 24 hours after bringing it to room temperature. The sodium hydride was then removed by filtration, washed with methylene chloride, and the washing combined with the filtrate. The solution was then worked up as in Example 1, yielding 1.32 g of product (1), a yield which was 91% of the theoretical.

EXAMPLE 6

The same procedure was followed as in Example 2 except that there was used as the amine 0.983 ml diisopropylethyl amine (an excess) and there was used only 0.2 ml trifluoroacetic anhydride. Two products were obtained, 90 mg of the same product as in Example 2 (79% yield based on anhydride) and 25 mg of the corresponding monoacylated product (14% yield based on anhydride):

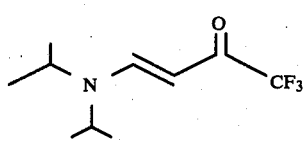

Analytical data for the product was as follows:

$^1$H NMR: ($\delta$, CDCl$_3$, Me$_4$Si standard): 7.95 (1H, d, J=12 Hz), 5.41) (1H, d, J=12 Hz), 3.97 (1H, septet, J=7 Hz), b.74 (1H, septet, J=7 Hz), 1.35 (6H, d, J=7 Hz), 1.26 (6H, d, J=7 Hz).

IR: 1650, 1570 (br.) cm$^{-1}$

UV: 313.5 $^{nm}$=$\lambda_{max}$, $\epsilon_{max}$=10,645

MS: m/e (rel %): 223 (45), 154 (100)

Analysis: Calculated for C$_{10}$H$_{16}$F$_3$NO: C: 53.80 H: 7.22 N: 7.17 F: 25.53. Found: C: 53.65 H: 7.29 N: 6.07 F: 25.05.

What is claimed is:

1. The method of oxidizing a tertiary amine selected from the group consisting of triethyl amine, diisopropyl ethyl amine, and N-methyl piperidine to form an acylated enamine, which method comprises mixing said amine with trihaloacetic anhydride or trihaloacetyl halide in a solvent inert to the reactants at a temperature from 0° to 100° C., and separating beta-trihaloacetylated alpha, beta-enamine from the reaction mixture.

2. The method as claimed in claim 1 in which the trihalo group is trifluoro and the halide is chloride.

3. The method as claimed in claim 1 in which additional inorganic base is added to the reaction mixture.

4. The method as claimed in claim 2 in which said amine is mixed with trifluoroacetic anhydride at a temperature from 0° to 25° C.

5. The method as claimed in claim 4 in which additional inorganic base is added to the reaction mixture.

6. The method as claimed in claim 5 in which said inorganic base is sodium hydride.

7. Mono- and di-trihaloacetylated alpha, beta-enamines made in accordance with the method of claim 1.

8. The method as claimed in claim 1 in which said tertiary amine is triethyl amine.

9. The method as claimed in claim 1 in which said tertiary amine is diisopropyl ethyl amine.

10. The method as claimed in claim 1 in which said tertiary amine is N-methyl piperidine.

* * * * *